US00PP10184P

United States Patent [19]

Kleinhanns

[11] Patent Number: Plant 10,184

[45] Date of Patent: Jan. 6, 1998

[54] DAHLIA PLANT NAMED BILIPI

[75] Inventor: Christoph Kleinhanns, Eisleben, Germany

[73] Assignee: Saatzucht Quedlinburg GmbH, Quedlinburg, Germany

[21] Appl. No.: 657,332

[22] Filed: Jun. 3, 1996

[51] Int. Cl.[6] ..... A01H 5/00

[52] U.S. Cl. ..... Plt./87.8

[58] Field of Search ..... Plt./87.8

*Primary Examiner*—James R. Feyrer

*Assistant Examiner*—Melissa L. Kimball

*Attorney, Agent, or Firm*—C. A. Whealy

[57] ABSTRACT

A distinct cultivar of Dahlia plant named Bilipi, characterized by its compact growth habit; small leaves and inflorescences that are proportional to the overall plant size; ease of propagation; and light purple ray florets with dark yellow disc florets.

2 Drawing Sheets

The present invention relates to a new and distinct cultivar of Dahlia plant, botanically known as *Dahlia hybrida*, and hereinafter referred to by the cultivar name Bilipi.

The new Dahlia is a product of a planned breeding program conducted by the inventor in Quedlinburg, Germany. The objective of the breeding program was to create new Dahlia cultivars having a compact growth habit suitable for 7 to 9-cm container production, small inflorescences, desirable inforescence colors, and inflorescences and foliage with good substance.

The new Dahlia originated from a cross made by the inventor of the inventor's proprietary Dahlia seedling selections. The cultivar Bilipi was discovered and selected by the inventor as a flowering plant within the progeny of this cross in a controlled environment in Quedlinburg, Gemany.

Asexual reproduction of the new Dahlia by terminal cuttings taken at Quedlinburg, Germany, has shown that the unique features of this new Dahlia are stable and reproduced true to type in successive generations.

The following traits have been repeatedly observed and are determined to be the unique characteristics of Bilipi. These characteristics in combination distinguish Bilipi as a new and distinct cultivar:

1. Compact growth habit, suitable for 7 to 9-cm contaniers. Plants do not require growth retardants.
2. Small leaves and inflorescences that are proportional to the overall plant size.
3. Excellent rooting and easy to propagate.
4. Light purple ray florets with dark yellow disc florets.

The new Dahlia has not been observed under all possible environmental conditions. The phenotype may vary somewhat with variations in environment such as temperature, daylength and light intensity, without, however, any variance in genotype.

Compared to the female parent, plants of the new Dahlia have smaller inflorescences. Plants of the new Dahlia differ from the male parent in ray floret color.

BRIEF DESCRIPTION OF THE DRAWINGS

The accompanying colored photographs illustrate the overall appearance of the new cultivar, showing the colors as true as it is reasonably possible to obtain in colored reproductions of this type.

The first photograph comprises a side perspective view of a typical flowering plant of Bilipi.

The upper photograph on the second sheet of photographs comprises a top perspective view of mature (left) and immature (right) leaves. The upper (top) and under (bottom) sides of the immature leaves are shown.

The lower photograph comprises a close-up view of inflorescences of Bilipi. Floret and foliage colors may appear different than the actual colors due to light reflectance.

In the following description, color references are made to The Royal Horticultural Society Colour Chart except where general terms of ordinary dictionary significance are used. The following observations and measurements describe plants grown in Quedlinburg, Germany, during the winter season under commercial practice in a glass-covered greenhouse with average night temperatures of 15C., average day temperatures of 20C., and light levels of 2,500 lux.

p0 Botanical classification: *Dahlia hybrida* cultivar Bilipi.

Commercial classification: Pot Dahlia.

Parentage:

*Male, or pollen, parent.*—Proprietary Dahlia seedling selection.

*Female, or seed, parent.*—Proprietary Dahlia seedling selection.

Propagation:

*Type.*—Terminal tip cuttings.

*Time to rooting.*—15 to 20 days with soil temperatures of 20C.

*Rooting habit.*—Propagates easily, roots fibrous and well-branched.

Plant description:

*Appearance.*—Perennial herbaceous potted plant. Bushy with stems upright. Freely branching, plants do not require pinching. Compact growth habit and moderate growth rate. Suitable for 7 to 9-cm containers. From a rooted cutting, six weeks are required to produce a flowering pot plant.

*Plant height.*—About 16 cm.

*Stem description.*—Internode length: About 2 to 2.5 cm. Diameter: About 3 mm. Color: 144B.

*Foliage description.*—Arrangement: Young foliage: Single. Fully expanded: Compound, trifoliate. Leaf size: Young foliage: Length: About 3 cm. Width: About 2 cm. Mature foliage: Length: About 6 cm. Width: About 3.5 cm. Leaf/leaflet shape: Ovate. Leaf/leaflet apex: Acuminate. Leaf/leaflet base: Attenuate. Leaf/leaflet margin: Slightly serrated. Leaf/leaflet texture: Smooth, glabrous. Petiole length: Young foliage: About 1.5 cm. Fully expanded: About 3 cm. Color: Young foliage upper surface: 137B. Young foliage under surface: 138B/138C. Fully expanded foliage upper surface: 137B. Fully expanded foliage under surface: 138B/138C. Petiole: 144B.

Flowering description:

*Appearance.*—Daisy inflorescence form. Inflorescences flat and borne on terminals above foliage, arising from leaf axils. Disc and ray florets arranged acropetally on a capitulum.

*Flowering response.*—Under natural conditions, plants flower continuous in the summer/autunm in the Northern Hemisphere. At other times of the year, inflorescence initiation and development can be induced under long day/short night conditions (less than 11 hours of darkness). Inflorescences persistent.

*Inflorescence size.*—Diameter: 3 to 4 cm. Depth (height): About 1.5 cm.

*Flower bud.*—Shape: Ovoid. Size: Length: About 5 mm. Diameter: About 7 mm. Color: 144B to 151C.

*Ray florets.*—Shape: Oblanceolate. Size: Length: About 15 mm. Width: 5 to 7 mm. Apex: Obtuse. Margin: Entire. Texture: Satiny, smooth and glabrous. Number of ray florets per inflorescence: 30 to 35, about three rows of florets. Color: Upper surface: 75D at base; darker, 80C/78C at center and distal end. Immature ray florets are initially yellow at base before developing light purple color. Under surface: 75D at base; darker, 80C/78C at center and distal end.

*Disc florets.*—Number of disc florets per inflorescence: About 50. Color: 14B.

*Peduncle.*—Aspect: Erect and strong. Length: 3.5 to 5 cm. Diameter: About 1 mm. Texture: Glabrous. Color: 144B.

*Sepals.*—Quantity per inflorescence: 5 to 6. Shape: Oblanceolate. Tip: Acute. Margin: Entire. Color: 137B.

*Reproductive organs.*—Androecium: Anther size: About 2 mm. Anther color: 14B. Pollen: 14B. Gynoecium: Style length: About 2 mm. Stigma color: 5D.

Disease resistance: No known Dahlia diseases observed to date on plants grown under commercial greenhouse conditions.

Seed production: Seed production has not been observed.

It is claimed:

1. A new and distinct cultivar of Dahlia plant named Bilipi, as illustrated and described.

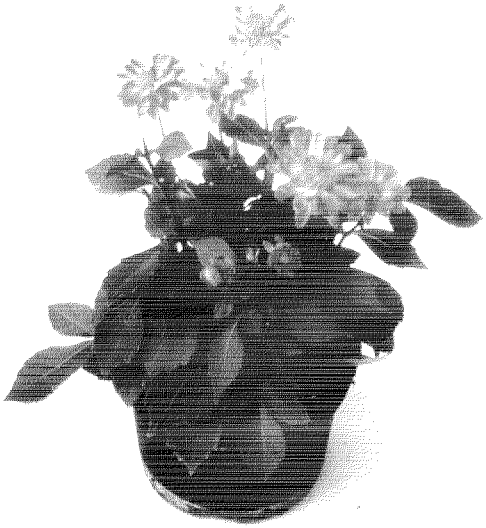

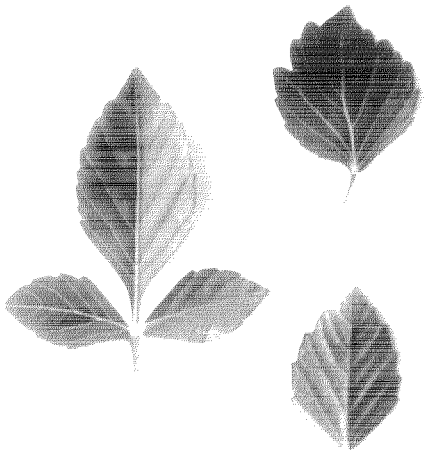
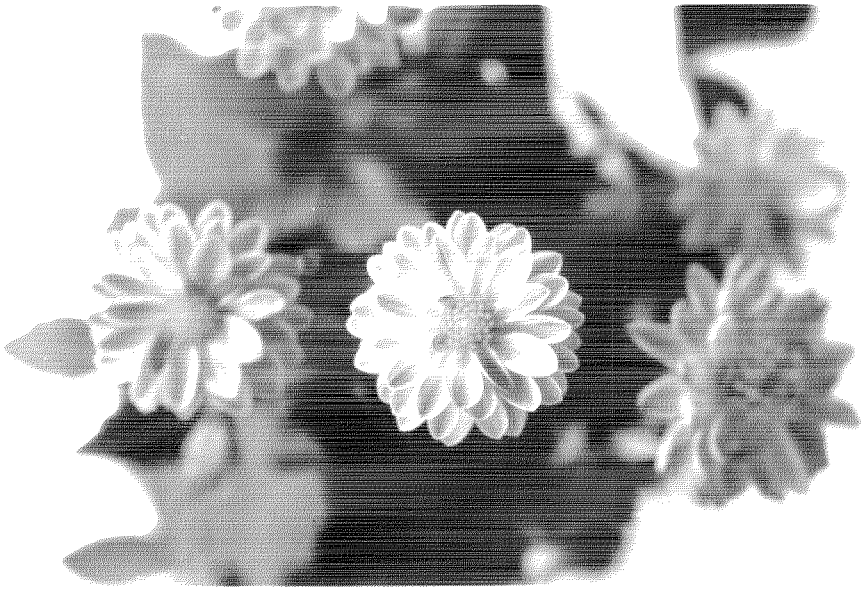

* * * * *